(12) United States Patent
Miros et al.

(10) Patent No.: US 7,837,638 B2
(45) Date of Patent: Nov. 23, 2010

(54) FLEXIBLE JOINT WRAP

(75) Inventors: Robert H J Miros, Fairfax, CA (US); Charlotte Hutter-Brock, Chico, CA (US)

(73) Assignee: CoolSystems, Inc., Alameda, CA (US)

( * ) Notice: Subject to any disclaimer, the term of this patent is extended or adjusted under 35 U.S.C. 154(b) by 670 days.

(21) Appl. No.: 11/707,419

(22) Filed: Feb. 13, 2007

(65) Prior Publication Data

US 2008/0195012 A1    Aug. 14, 2008

(51) Int. Cl.
*A61F 5/00* (2006.01)
(52) U.S. Cl. .............................. 602/13; 602/2; 602/60; 602/61; 607/108; 607/112
(58) Field of Classification Search ......... 607/108–112; 602/2, 13, 3
See application file for complete search history.

(56) References Cited

U.S. PATENT DOCUMENTS 1,958,899 A    5/1934    MacAdams (Continued)

FOREIGN PATENT DOCUMENTS

DE    3343664    3/1985

(Continued)

OTHER PUBLICATIONS

PCT International Search Report.

(Continued)

*Primary Examiner*—Kim M Lewis
(74) *Attorney, Agent, or Firm*—Shay Glenn LLP

(57) ABSTRACT

A flexible joint wrap includes a heat exchange bladder, which provides fluid circulation and compression to a joint. The joint wrap includes upper and lower sections for attachment above and below a joint. The bladder has an opening at a center section which provides flexibility of the bladder. The heat exchange bladder may be enclosed in a removable cover designed to conform to the shape of the bladder. The cover and bladder are formed with an opening in alignment with the joint to provide flexibility to the wrap. The cover may be formed of a fluid repellant inner lining to prevent fluid from the joint from soiling the bladder. The cover may further comprise a nylon loop outer surface to allow the upper and lower sections to be easily attached and adjusted.

10 Claims, 7 Drawing Sheets

U.S. PATENT DOCUMENTS

| | | |
|---|---|---|
| 2,413,386 A | 12/1946 | Schulz |
| 2,510,125 A | 6/1950 | Meakin |
| 2,531,074 A | 11/1950 | Miller |
| 2,540,547 A | 2/1951 | Rodert |
| 2,608,690 A | 9/1952 | Kolb et al. |
| 2,703,770 A | 3/1955 | Melzer |
| 2,726,658 A | 12/1955 | Chessey |
| 3,261,042 A | 7/1966 | Baker |
| 3,320,682 A | 5/1967 | Silman |
| 3,354,898 A | 11/1967 | Barnes |
| 3,561,435 A | 2/1971 | Nicholson |
| 3,738,367 A | 6/1973 | Hardy |
| 3,744,555 A | 7/1973 | Fletcher et al. |
| 3,830,676 A | 8/1974 | Elkins |
| 3,871,381 A | 3/1975 | Roslonski |
| 3,901,225 A | 8/1975 | Sconce |
| 3,993,053 A | 11/1976 | Grossan |
| 4,026,299 A | 5/1977 | Sauder |
| 4,116,476 A | 9/1978 | Porter et al. |
| 4,118,946 A | 10/1978 | Tubin |
| 4,147,921 A | 4/1979 | Walter et al. |
| 4,149,529 A | 4/1979 | Copeland et al. |
| 4,149,541 A | 4/1979 | Gammons et al. |
| 4,194,247 A | 3/1980 | Melander |
| 4,338,944 A | 7/1982 | Arkans |
| 4,412,648 A | 11/1983 | Ford et al. |
| 4,436,125 A | 3/1984 | Blenkush |
| 4,471,759 A | 9/1984 | Anderson et al. |
| 4,478,436 A | 10/1984 | Hashimoto |
| 4,547,906 A | 10/1985 | Nishida |
| 4,597,384 A | 7/1986 | Whitney |
| 4,678,027 A | 7/1987 | Shirey et al. |
| 4,691,762 A | 9/1987 | Elkins et al. |
| 4,718,429 A | 1/1988 | Smidt |
| 4,738,119 A | 4/1988 | Zafred |
| 4,753,268 A | 6/1988 | Palau |
| 4,765,338 A | 8/1988 | Turner et al. |
| 4,844,072 A | 7/1989 | French et al. |
| 4,884,304 A | 12/1989 | Elkins |
| 4,925,603 A | 5/1990 | Nambu |
| 4,955,435 A | 9/1990 | Shuster et al. |
| 4,964,282 A | 10/1990 | Wagner |
| 4,976,262 A | 12/1990 | Palmacci |
| 5,002,270 A | 3/1991 | Shine |
| 5,014,695 A | 5/1991 | Benak et al. |
| 5,022,109 A | 6/1991 | Pekar |
| 5,033,136 A | 7/1991 | Elkins |
| 5,052,725 A | 10/1991 | Meyer et al. |
| 5,072,875 A | 12/1991 | Zacoi |
| 5,074,285 A | 12/1991 | Wright |
| 5,076,068 A | 12/1991 | Mikhail |
| 5,080,089 A | 1/1992 | Mason et al. |
| 5,080,166 A | 1/1992 | Haugeneder |
| 5,086,771 A | 2/1992 | Molloy |
| 5,097,829 A | 3/1992 | Quisenberry |
| 5,104,158 A | 4/1992 | Meyer et al. |
| 5,113,877 A | 5/1992 | Johnson, Jr. et al. |
| 5,163,425 A | 11/1992 | Nambu et al. |
| 5,172,689 A | 12/1992 | Wright |
| 5,201,552 A | 4/1993 | Hohmann et al. |
| 5,230,335 A | 7/1993 | Johnson, Jr. et al. |
| 5,241,951 A | 9/1993 | Mason et al. |
| 5,243,706 A | 9/1993 | Frim et al. |
| 5,269,369 A | 12/1993 | Faghri |
| 5,294,156 A | 3/1994 | Kumazaki et al. |
| 5,314,455 A | 5/1994 | Johnson, Jr. et al. |
| 5,316,547 A | 5/1994 | Gildersleeve |
| 5,353,605 A | 10/1994 | Naaman |
| 5,354,101 A | 10/1994 | Anderson, Jr. |
| 5,354,103 A | 10/1994 | Torrence et al. |
| 5,383,689 A | 1/1995 | Wolfe, Sr. |
| RE34,883 E | 3/1995 | Grim |
| 5,395,399 A | 3/1995 | Rosenwald |
| 5,407,421 A | 4/1995 | Goldsmith |
| 5,411,541 A | 5/1995 | Bell et al. |
| 5,415,625 A | 5/1995 | Cassford et al. |
| 5,417,720 A | 5/1995 | Mason |
| 5,427,577 A | 6/1995 | Picchietti et al. |
| 5,441,533 A | 8/1995 | Johnson et al. |
| 5,449,379 A | 9/1995 | Hadtke |
| 5,451,201 A | 9/1995 | Prengler |
| 5,466,250 A | 11/1995 | Johnson, Jr. et al. |
| 5,470,353 A | 11/1995 | Jensen |
| 5,476,489 A | 12/1995 | Koewler |
| 5,494,074 A | 2/1996 | Ramacier, Jr. et al. |
| 5,496,358 A | 3/1996 | Rosenwald |
| 5,520,622 A | 5/1996 | Bastyr et al. |
| 5,524,293 A | 6/1996 | Kung |
| 5,527,268 A | 6/1996 | Gildersleeve et al. |
| 5,533,354 A | 7/1996 | Pirkle |
| 5,539,934 A | 7/1996 | Ponder |
| 5,554,119 A | 9/1996 | Harrison et al. |
| 5,556,138 A | 9/1996 | Nakajima et al. |
| 5,564,124 A | 10/1996 | Elsherif et al. |
| 5,630,328 A | 5/1997 | Hise et al. |
| 5,645,671 A | 7/1997 | Tillinghast |
| 5,683,118 A | 11/1997 | Slocum |
| 5,792,216 A | 8/1998 | Kappel |
| 5,833,638 A | 11/1998 | Nelson |
| 5,865,841 A | 2/1999 | Kolen et al. |
| 5,868,690 A | 2/1999 | Eischen, Sr. |
| 5,913,885 A | 6/1999 | Klatz et al. |
| 5,920,934 A | 7/1999 | Hannagan et al. |
| 5,967,225 A | 10/1999 | Jenkins |
| 5,968,072 A | 10/1999 | Hite et al. |
| 5,970,519 A | 10/1999 | Weber |
| 5,980,561 A | 11/1999 | Kolen et al. |
| 5,984,885 A | 11/1999 | Gaylord, Jr. et al. |
| 5,989,285 A | 11/1999 | DeVilbiss et al. |
| 5,992,459 A | 11/1999 | Sugita et al. |
| 6,030,412 A | 2/2000 | Klatz et al. |
| 6,036,107 A | 3/2000 | Aspen et al. |
| 6,053,169 A | 4/2000 | Hunt |
| 6,083,256 A | 7/2000 | Der Ovanesian |
| 6,105,382 A | 8/2000 | Reason |
| 6,109,338 A | 8/2000 | Butzer |
| 6,117,164 A | 9/2000 | Gildersleeve |
| 6,146,413 A | 11/2000 | Harman |
| 6,156,059 A | 12/2000 | Olofsson |
| 6,178,562 B1 | 1/2001 | Elkins |
| 6,261,314 B1 | 7/2001 | Rich |
| 6,306,112 B2 | 10/2001 | Bird |
| 6,328,276 B1 | 12/2001 | Falch et al. |
| 6,352,550 B1 | 3/2002 | Gildersleeve et al. |
| 6,354,635 B1 | 3/2002 | Dyson et al. |
| 6,361,514 B1 | 3/2002 | Brown et al. |
| 6,368,357 B1 | 4/2002 | Schon et al. |
| 6,371,976 B1 | 4/2002 | Vrzalik et al. |
| 6,382,678 B1 | 5/2002 | Field et al. |
| 6,443,498 B1 | 9/2002 | Liao |
| 6,547,284 B2 | 4/2003 | Rose et al. |
| 6,551,347 B1 | 4/2003 | Elkins |
| 6,551,348 B1 | 4/2003 | Blalock et al. |
| 6,645,232 B2 | 11/2003 | Carson |
| 6,695,872 B2 | 2/2004 | Elkins |
| 6,823,682 B2 | 11/2004 | Jenkins et al. |
| 6,871,878 B2 | 3/2005 | Miros |
| 6,926,311 B2 | 8/2005 | Chang et al. |
| 6,942,015 B1 | 9/2005 | Jenkins |
| 7,008,445 B2 | 3/2006 | Lennox |
| 7,107,629 B2 | 9/2006 | Miros et al. |
| 7,198,093 B1 | 4/2007 | Elkins |
| 7,306,568 B2 | 12/2007 | Diana |
| 7,434,844 B2 | 10/2008 | Kao |

| | | | |
|---|---|---|---|
| 7,448,653 B2 | 11/2008 | Jensen et al. | |
| 7,490,620 B2 | 2/2009 | Tesluk et al. | |
| 2001/0018604 A1 | 8/2001 | Elkins | |
| 2001/0034545 A1 | 10/2001 | Elkins | |
| 2001/0034546 A1 | 10/2001 | Elkins | |
| 2001/0039439 A1 | 11/2001 | Elkins et al. | |
| 2002/0019657 A1 | 2/2002 | Elkins | |
| 2004/0167594 A1 | 8/2004 | Elkins | |
| 2005/0143796 A1 | 6/2005 | Augustine et al. | |
| 2005/0143797 A1 | 6/2005 | Parish et al. | |
| 2005/0256556 A1 | 11/2005 | Shirrmacher | |
| 2006/0200057 A1 | 9/2006 | Sterling | |
| 2007/0161932 A1 | 7/2007 | Pick et al. | |
| 2007/0282230 A1 | 12/2007 | Valderrabano et al. | |
| 2008/0058911 A1 | 3/2008 | Parish et al. | |
| 2009/0005841 A1 | 1/2009 | Schirrmacher et al. | |
| 2009/0066079 A1 | 3/2009 | Miros et al. | |

FOREIGN PATENT DOCUMENTS

| | | |
|---|---|---|
| EP | 1329676 A1 | 7/2003 |
| IT | 330552 | 10/1935 |
| WO | WO92/13506 A1 | 8/1992 |
| WO | WO92/15263 A1 | 9/1992 |
| WO | WO94/09732 A1 | 5/1994 |
| WO | WO96/26693 A1 | 9/1996 |
| WO | WO98/07397 A1 | 2/1998 |
| WO | WO99/44552 A1 | 9/1999 |
| WO | WO00/23016 A1 | 4/2000 |
| WO | WO00/55542 A1 | 9/2000 |
| WO | WO00/67685 A1 | 11/2000 |

OTHER PUBLICATIONS

Elkins, U.S. Appl. No. 09/173,637 entitled "Compliant heat exchange splint and control unit," filed Oct. 16, 1998.

Lowe et al.; U.S. Appl. No. 12/329,461 entitled "Cooling system having bypass valve to regulate fluid flow," filed Dec. 5, 2009.

Tomlinson et al.; U.S. Appl. No. 12/329,481 entitled "Therapeutic cooling and/or heating system including a thermo-conductive material," filed Dec. 5, 2009.

BioCompression Systems, Inc. (Moonachie, NJ); Product literature for Sequential Circulators; 15 pgs.

FLEXIBLE JOINT WRAP

BACKGROUND OF THE INVENTION

1. Field of the Invention

The present invention relates generally to a joint wrap allowing flexible movement of the joint, such as a knee or elbow.

2. Description of the Related Art

It is common to apply cold and compression to a traumatized area of a human body to facilitate healing, and to prevent unwanted consequences of the trauma. In fact, the acronym RICE (Rest, Ice, Compression and Elevation) is now used by many in the field. For example, cold packing with ice bags or the like traditionally are used to provide deep core cooling of a body part. In addition, elastic wraps are often applied to provide compression. However, these traditional techniques are uncontrollable. For example, the temperature of an ice pack will change when the ice melts, and the application of elastic wraps and, consequently the pressure provided thereby, varies considerably—even when the wrappers are experienced. Because of these and other difficulties, many have turned to more complicated arrangements which include cooling units for maintaining a desired temperature through a heat exchanger. Some of these cooling units also provide compressive pressure. Active cooling arrangements for humans are used, or contemplated for use, in physical therapy, pre-game conditioning, minor injury care, and so forth.

Many control units also produce and supply an air or other gas pressure needed to apply pressure to a body part and to press the heat exchange liquid toward such body part. This air pressure is directed to another compliant bladder of the therapy component, which air pressure bladder overlays the liquid bladder to press such liquid bladder against the body part to be subjected to heat exchange, as well as apply compression to the body part to reduce edema.

As can be seen, a commonly used external therapy component uses a pair of compliant bladders to contain fluids; that is, it preferably has both a compliant bladder for containing a circulating heat exchange liquid and a gas pressure bladder which overlays the liquid bladder for inhibiting edema and for pressing the liquid bladder against the body part to be subjected to heat exchange. One problem is that in many therapy component configurations of this nature, the gas pressure bladder tends to "balloon" or, in other words, expand to a much greater degree than is desired. This unwanted expansion can be the cause of several problems. For one, it can actually pull away from the body part some or all of the conformal heat exchange bladder. For another, it can reduce its edema inhibition ability, as well as reduce the desired effect of pressing the heat exchange bladder into contact with the body part.

More recently, physicians often prescribe Continuous Passive Motion (CPM) exercise for a patient's knee following surgery. This often involves the use of an automated device to flex the knee back and forth for up to several days to insure that the knee heals correctly following surgery.

However, the use of a CPM device following surgery often precludes the use of a cooling and compression wrap, since the current wraps are unable to flex properly, while still providing sufficient compression. For example, as shown in FIGS. 1(A) and 1(B), a prior cooling wrap comprises a wrap generally covering a top portion of a patient's knee area, and affixed via Velcro™ fasteners or the like at positions above and below the knee. However, such a configuration lacks any flexibility, making it unsuitable for use with CPM therapy.

Also, as shown in FIGS. 2(A) and 2(B), a prior knee wrap design provides additional flexibility at the knee, but due to its shape, does not provide adequate compression against the knee or the side of the knee.

SUMMARY OF THE INVENTION

In one embodiment, the present invention is a flexible, articulated joint wrap that provides fluid circulation and compression, while allowing the joint to flex. The wrap may configured, for example, as a separate heat exchange bladder and cover. The bladder may comprise separate chambers for fluid circulation and compression. The bladder may further comprise and upper section and a lower section for attaching the wrap above and below a joint. The bladder may have a center section having an opening that aligns with the outer joint, for example, with the patella on a knee. This allows the bladder to flex with the movement of the joint. The cover may be configured to conform to the shape of the bladder.

In one embodiment, the cover comprises an outer material of nylon loop, lined with a fluid repellant material, such as urethane. The cover may comprise an opening on the top and bottom of the cover which align with the opening in the bladder. Additionally, two tabs having Velcro™ ends are attached to the bottom opening. When assembled, the tabs are positioned through the bottom opening, through the opening in the bladder, through the top opening and attached via the Velcro™ ends to the top of the cover.

The bladder and cover may comprise an upper section and lower section, with each section having two wings. Wings on one side of the cover may be enclosed, with the wings on the opposite side open such that the bladder wings on the open side are exposed to allow attachment via Velcro™ strips on the ends. The cover may further comprise an opening for a hose coupling assembly attached to the bladder. In addition, a padded extension on the cover extends from the cover to protect a wearer from the hose coupling assembly.

The opening in the bladder may be configured as a vertical slit. The opening may further comprise a second slit oriented perpendicular to the first slit. These slits provide flexibility for movement of the joint, even when the bladder is inflated and applying compressive force to the area around the joint.

As described herein, a joint wrap configured according to the present teachings provides a flexible joint wrap, suitable for use with a Continuous Passive Motion device. The outer cover may be disposed of after use, allowing the bladder to be reused. The design of the joint wrap provides circumferential compression around the joint area, while still allowing for flexible movement of the joint.

In an alternative embodiment, the knee wrap may comprise just the bladder, with complementary Velcro™ type material placed to secure attachment of the bladder to a joint.

BRIEF DESCRIPTION OF THE DRAWINGS

The present invention will be readily understood by the following detailed description in conjunction with the accompanying drawings, wherein like reference numerals designate like structural elements, and in which.

DETAILED DESCRIPTION OF THE INVENTION

The following description is provided to enable any person skilled in the art to make and use the invention and sets forth the best modes contemplated by the inventor for carrying out the invention. Various modifications, however, will remain readily apparent to those skilled in the art. Any and all such modifications, equivalents and alternatives are intended to fall within the spirit and scope of the present invention.

Figure 1A:
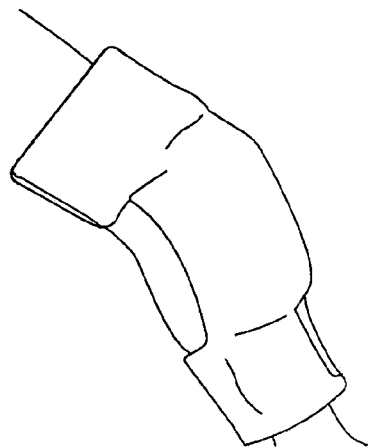
FIGS. 1(A) and 1(B) illustrate a prior art knee wrap.
Figure 1B:
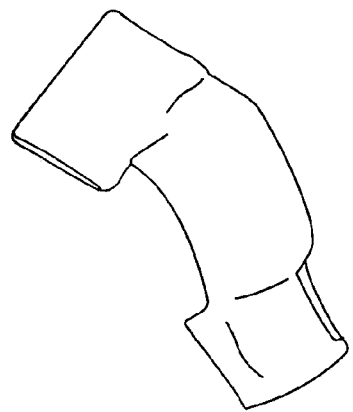
Figure 2A:
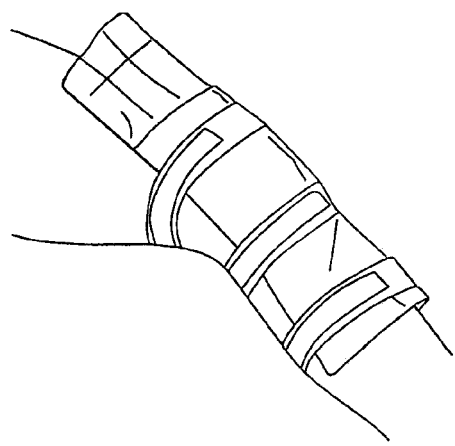
FIGS. 2(A) and 2(B) illustrate a prior art knee wrap.
Figure 2B:
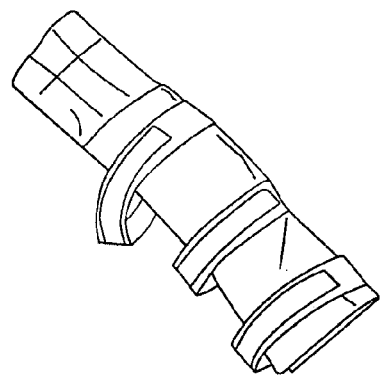
Figure 3:
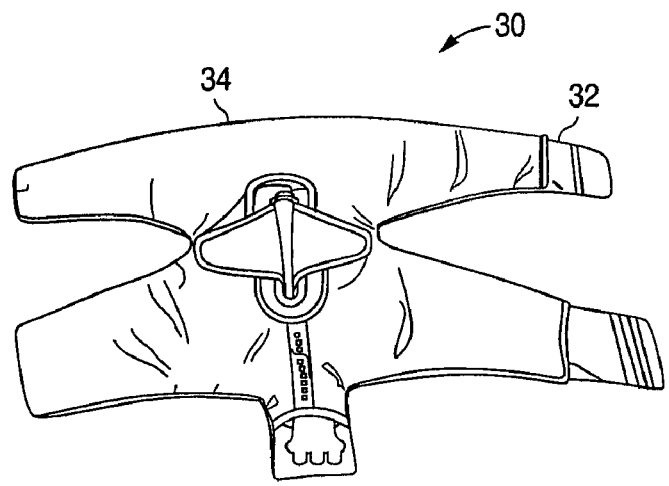
FIG. 3 illustrates an embodiment of the present invention.

An embodiment of a flexible knee wrap 30 according to the present invention is shown in FIG. 3. While the present invention is described herein with respect to a specific embodiment suitable for use as a knee wrap, other configurations may be adapted for use with other joints, such as elbows or shoulders. The present invention is thus not limited to the specific knee wrap described herein, but is applicable to other configurations as well.

The knee wrap 30 may comprise a separate heat exchange bladder 32 and a cover 34. The heat exchange bladder 32 preferably provides both fluid circulation (i.e. cooling) and compression, and may generally be constructed as taught by U.S. Pat. No. 6,695,872, entitled THERAPY COMPONENT OF AN ANIMATE BODY HEAT EXCHANGER, the disclosure of which is herein incorporated by reference. A heat exchange bladder of the present invention may thus have separate chambers for fluid circulation, and for compression. The knee wrap 30 is preferably formed in articulated sections, allowing for flexible movement of the knee, while still providing a snug fit on a wearer's knee and leg.

Figure 4B:
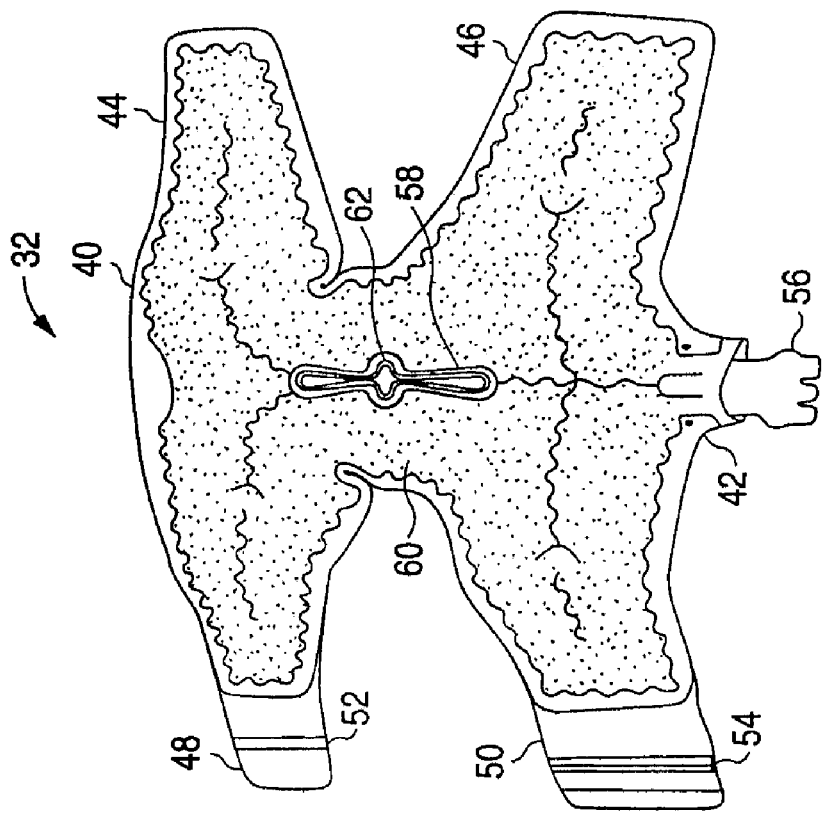
FIGS. 4(A) and 4(B) illustrate a top view and a bottom view, respectively, according to one embodiment of a bladder of the present invention.
Figure 4A:
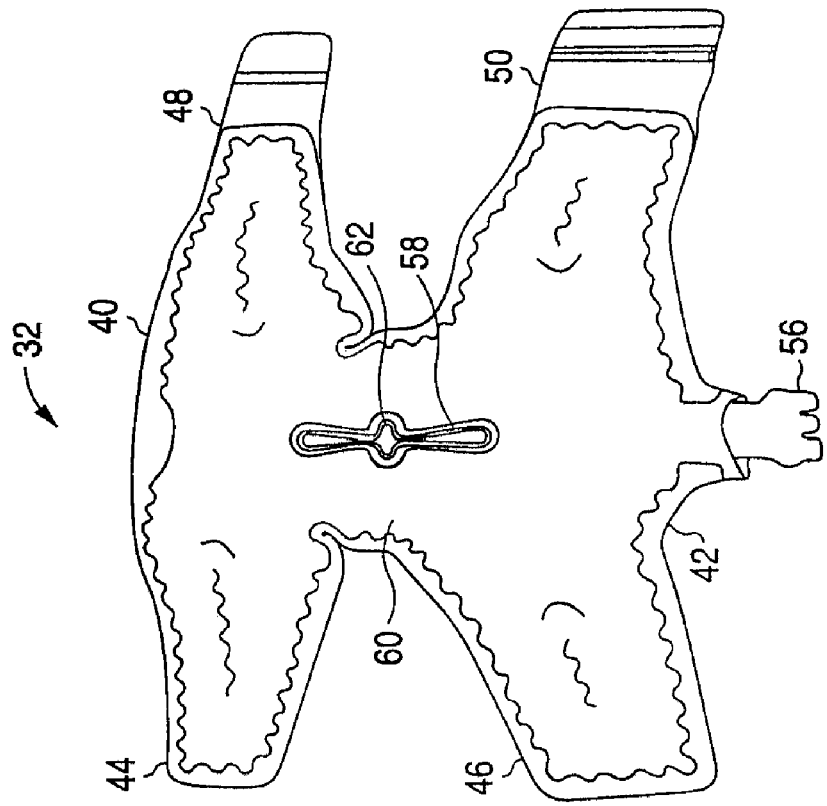

As illustrated in FIGS. 4(A) and 4(B), the bladder 32 is generally configured having an upper section 40 and a lower section 42. FIG. 4(A) illustrates a top view, and FIG. 4(B) illustrates a bottom view of the bladder 32. Each of the upper and lower sections 40, 42 includes two wing portions 44, 48 and 46, 50 respectively. The upper wing portions 44, 48 wrap around a leg above the knee. Preferably one wing 48 has "hook" type Velcro™ material 52 on the bottom side of an end for attachment. Similarly, the lower section 42 has two wing portions 46, 50, which wrap around a wearer's leg at a position below the knee. Preferably, one of the lower wings 50 has hook-type Velcro™ material 54 on a bottom side of one end. The lower portion 42 also includes a hose coupling assembly 56 for attachment to a cooling and compression control unit (not shown).

To provide for flexible extension of the knee, the bladder 32 is designed with a generally elongated slit 58 in the center of a body portion 60 of the bladder 32. The slit 58 is also used to attach the cover (as described below). No specific length or shape of the slit 58 is required, as long as it provides for flexible movement of the bladder 32 when attached to a wearer' knee, while still providing sufficient coverage to provide adequate cooling and compression. A generally circular or rectangular opening, or other similar openings, could be satisfactorily utilized as well. In a preferred embodiment, the elongated slit further includes a short perpendicular slit 62 in the center to provide for additional flexibility of the bladder 32.

In order to protect the bladder 32, especially from any fluids which may be present in the location of a post-operative knee, a cover 34 is provided which is specifically designed to cooperate with the bladder 32, while still maintaining flexibility of the knee wrap 30. The cover is further illustrated in FIGS. 5(A) and 5(B), wherein FIG. 5(A) is a top view and FIG. 5(B) is a bottom view of the cover 34. As illustrated in these figures, the cover 34 generally conforms to the shape of the bladder 32, and includes upper 70 and lower 72 sections having wing portions 74, 78 and 76, 80, respectively, corresponding to the general shape of the bladder 32. The wing portions 74, 76 on one side of the bladder are enclosed, whereas the wing portions 78. 80 on the other side are open at the ends. On the top of the cover 34, there is an opening 82, which is used to insert the bladder 32 during assembly (described below).

The bottom of the cover 34 includes a smaller opening 84 generally aligned with the opening 82 on the top. Attached to each side of the opening 84 on the bottom of the cover are two tabs 86, 88. As illustrated in FIGS. 5(A) and 5(B), the tabs 86, 88 are attached to the smaller opening 84 on the bottom of the cover, and fold around through the larger opening 82 on the top of the cover 34. In a preferred embodiment, the tabs 86, 88 are sewn into each side of the smaller opening 82.

Figure 5C:
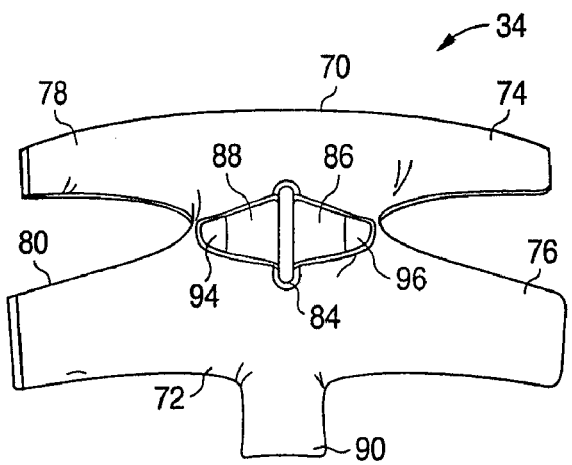
FIG. 5(C) illustrates a bottom view of the cover of FIGS. 5(A) and 5(B) with the tabs.
Figure 6E:
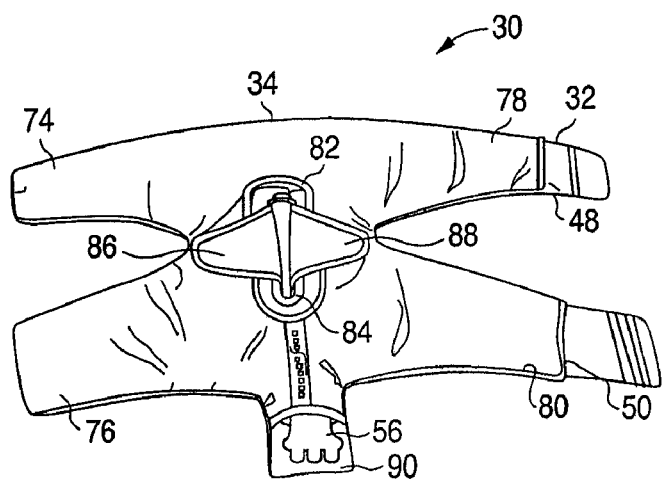
FIGS. 6(A)-6(E) illustrates the steps of placing the bladder of FIG. 4 into the cover of FIG. 5.
Figure 5B:
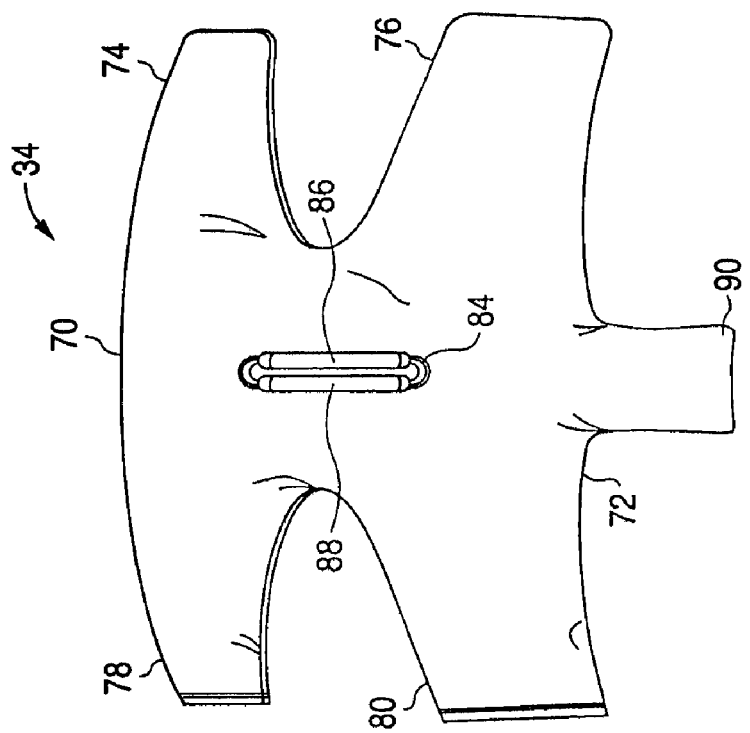
FIGS. 5(A) and 5(B) illustrate a top view and a bottom view, respectively, according to one embodiment of a cover of the present invention.
Figure 5A:
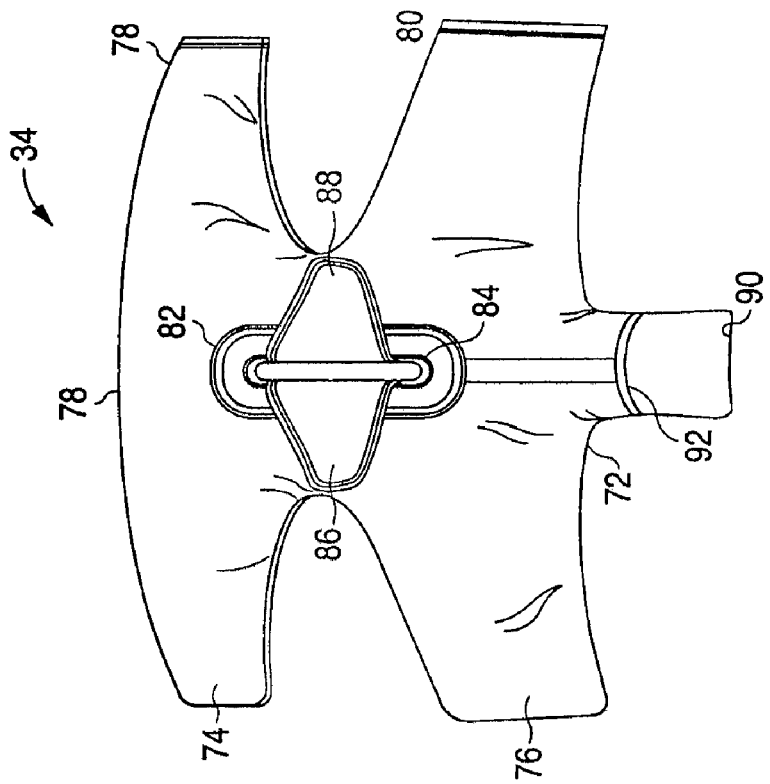

As illustrated in FIG. 5(C), the tabs 86, 88 are shown from the bottom of the cover. Each tab 86, 88 include a hook-type Velcro™ fastener 96, 94, respectively, on the ends.

The lower portion of the cover 34 includes a padded extension 90 having an opening 92 for receiving the hose coupling assembly 56 of the bladder 32. The padded portion 90 protects a wearer's leg from any irritation that may be caused by direct contact with the hose coupling assembly 56 during use of the knee wrap 30. The cover may be configured without the padded portion, if desired.

In a preferred embodiment, the cover 34 is made from a nylon loop knit (such as Velcro™ material), or similar material, laminated with a fluid repellant backing, such as urethane. In construction, the urethane backing is placed on the inside of the cover in contact with the bladder 32. The urethane backing helps block any fluids from coming in contact with the bladder 32. By constructing the outer shell of the cover 34 from a nylon loop knit, corresponding Velcro™ hook material is easily attached and removed along any portion of the cover 34, which provides for easy placement and adjustment on a wearer's knee. However, one could configure the cover out of different material, and provide strips or bands of loop type material only on the opposite wings, if desired.

Figure 6A:
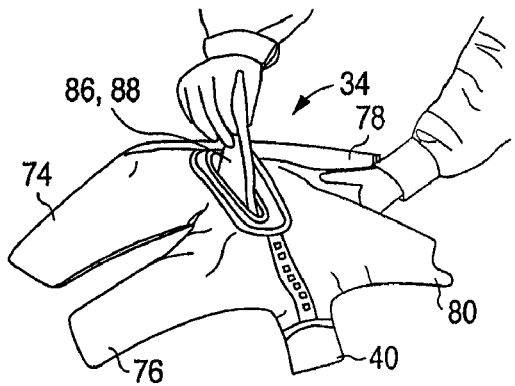
Figure 6B:
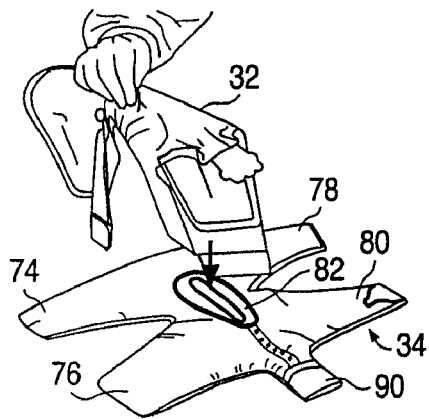
Figure 6C:
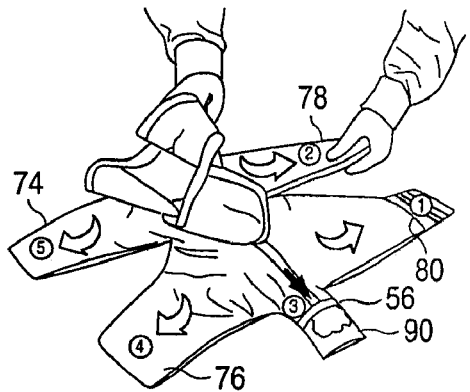
Figure 6D:
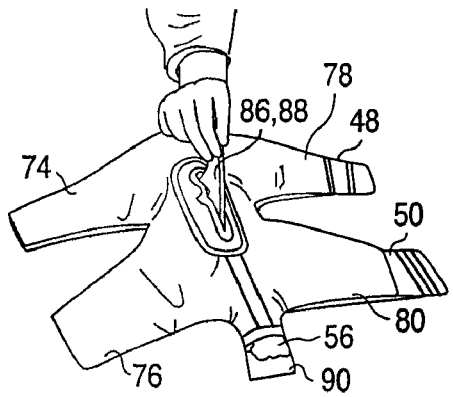

FIGS. 6(A)-6(E) illustrate the steps required to place the bladder 32 inside the cover 34. In FIG. 6(A), the Velcro™-tipped tabs 86, 88 are detached from the top of the cover 34 and pushed back through both the larger opening 82 on the top, and the smaller opening 84 on the bottom. Next, as illustrated in FIG. 6(B), the heat exchange bladder 32 is inserted through the larger opening 82 on the top of the cover. The bottom of the bladder 32 is placed face down, and the hose coupling assembly 56 is aligned with the padded extension opening 92, as the bladder 32 is inserted into the opening 82. As shown in FIG. 6(C), the Velcro™-tipped ends 48, 50 of the bladder 32 are pulled through the open wing ends 78, 80 of the cover 34 (positions 1 and 2 in the figure). The hose coupling assembly 56 is pulled through the opening 92 (position 3). The opposite wings 44, 46 are then placed into their corresponding cover wings 74, 76 respectively (positions 4 and 5). Finally, as illustrated in FIG. 6(D), the tabs 86, 88 are pulled through the bottom opening 82, through the slit 58 in the bladder 32, and through the larger opening 84 on the top of the cover 34. The Velcro™ tips on the tabs 86, 88 are then pressed against the loop material of the cover to securely attach the cover 34 and bladder 32 together. The final assembly is shown again in FIG. 6(E), which corresponds to the view of FIG. 3.

Figure 7A:
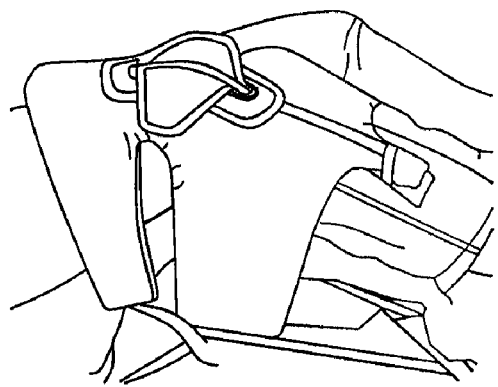
FIGS. 7(A)-7(E) illustrates the attachment of a knee wrap according to one embodiment of the present invention to a wearer's knee and leg.

FIGS. 7(A)-7(E) illustrate the attachment of the knee wrap to a user's leg. As shown in FIG. 7(A), the center slot is placed over a user's patella, with the knee slightly bent. Preferably, the hose coupling assembly 56 is oriented towards the user's foot to minimize distraction from the control unit hoses. However, the knee wrap of the present invention may be configured to attach the control unit hoses at a user's thigh, or other suitable location, as desired.

Figure 7B:
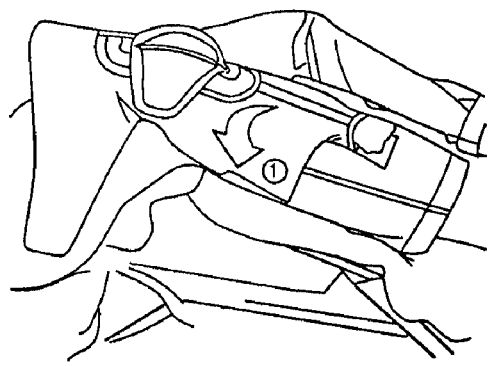
Figure 7C:
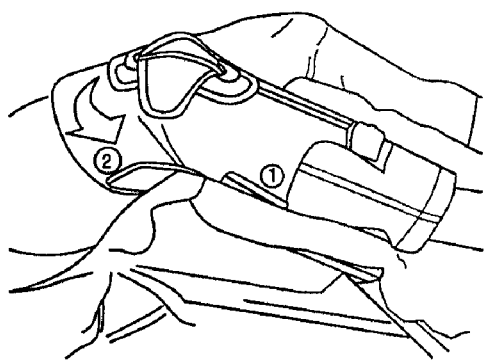
Figure 7D:
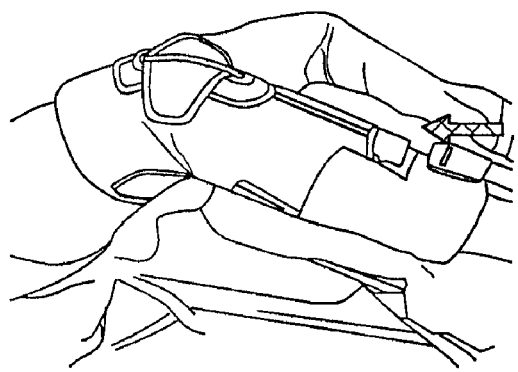
Figure 7E:
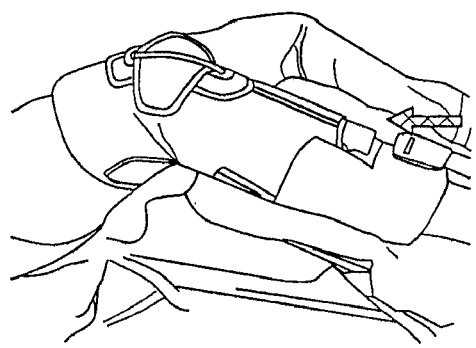

In FIG. 7(B), the wing portion 50 is wrapped under the user's leg, and is attached to the opposite wing (step 1). Since the entire surface of the cover 34 is loop material, the Velcro™ 54 on the wing portion 50 is easily attached and adjusted for fit and comfort. Similarly, as shown in FIG. 7(C), the upper wing 48 is wrapped under the user's thigh, and the Velcro™ material 52 is attached to the cover 34 (step 2). When properly aligned, there is an opening formed behind the knee, which allows the knee to flex. Finally, a mating hose assembly is attached to the hose coupling assembly 56 on the knee wrap 30 (FIG. 7(D)). The attached knee wrap is illustrated in FIG. 7(E).

Figure 8A:
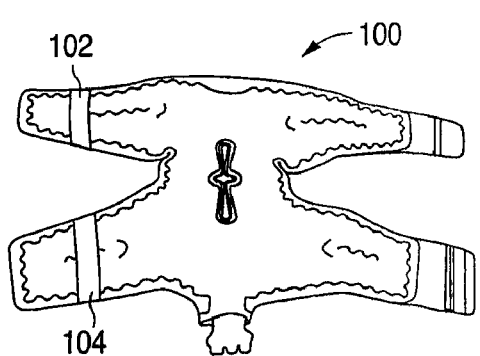
FIGS. 8(A) and 8(B) illustrate an alternative embodiment of the present invention in which a heat exchange bladder is used without a cover.
Figure 8B:
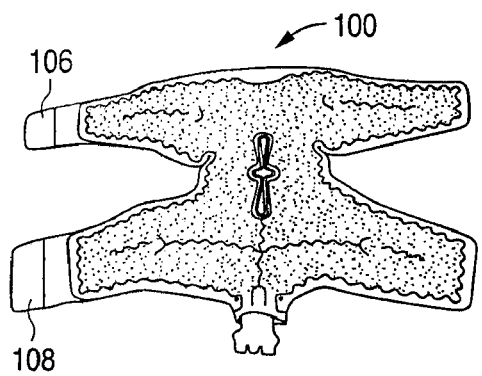

While the present invention has been described herein with respect to a preferred embodiment having a removable cover, a flexible knee wrap can be constructed utilizing just the heat exchange bladder. In this alternative embodiment, as shown in FIGS. 8(A) and 8(B), the bladder 100 includes complementary Velcro material on each respective upper wing 102, 106 and lower wing 104, 108. FIG. 8(A) shows a top view of the bladder 100 with Velcro™ type material on the wings on one side, and FIG. 8(B) shows a bottom view of the bladder 100 with Velcro™ type material on the wings on an opposite side. Thus, the bladder 100 can be attached directly to the joint, without the use of a cover. Moreover, the outer shell of the bladder could be covered with Velcro™ type material to facilitate attachment and adjustment.

As previously mentioned, the present invention is particularly useful for cooling and compression of the knee when a user is using a CPM device to flex the knee. As the CPM machine flexes the knee, the unique design of the present invention provides sufficient flexibility to not interfere with the intended benefits of the CPM device. The present knee wrap also provides excellent coverage of the knee and surrounding area to insure proper cooling and compression. Specifically, the present design provides greater circumferential compression around the knee area than is available with the prior art wraps noted above. A wrap designed according to the present invention provides greater compression around the leg (or limb) using 'non-elastic' construction, thus imparting compression in toward the limb rather than stretching away from the limb (as does the prior art).

By forming the present knee wrap with a separate heat exchange bladder and cover, the cover can be removed and disposed of after use, allowing the bladder to be used again by other patients. Also, a two layer construction provides better wear, and is more comfortable to a user.

Those skilled in the art will appreciate that various adaptations and modifications of the just-described preferred embodiments can be configured without departing from the scope and spirit of the invention. Therefore, it is to be understood that, within the scope of the appended claims, the invention may be practiced other than as specifically described herein.

What is claimed is:

1. A flexible joint wrap comprising:
    a heat exchange bladder comprising:
        an upper bladder section having a first upper bladder wing and a second upper bladder wing;
        a lower bladder section having a first lower bladder wing and a second lower bladder wing;
        a center body bladder section between the upper and lower bladder sections having a first opening; and
        a hose coupling assembly attached to the bladder;
    a cover shaped to conform to a shape of the bladder comprising:
        an upper cover section having a first upper cover wing and a second upper cover wing;
        a lower cover section having a first lower cover wing and a second lower cover wing;
        a center body cover section between the upper and lower cover sections having a first opening on a top of the cover, and a second opening on a bottom of the cover;
        a first tab and a second tab connected to the second opening on the bottom of the cover; and
        a hose coupling assembly opening;
    wherein when the bladder is in the cover, the first and second upper and lower bladder wings of the bladder align with the first and second upper and lower cover wings of the cover, the hose coupling assembly of the bladder aligns with the hose coupling assembly opening of the cover, and the tabs are folded over a top of the cover from the bottom of the cover, through the opening in the center section of the bladder.

2. The joint wrap of claim 1, wherein one upper wing on the upper cover section is enclosed, and the other upper wing has an opening for a bladder wing; and one lower wing on the lower cover section is enclosed, and the other lower wing has an opening for a bladder wing.

3. The joint wrap of claim 2, wherein the cover comprises an inner fluid repellant material, and nylon loop material on at least a portion of the outer enclosed cover wings.

4. The joint wrap of claim 2, wherein the cover comprises an outer material of nylon loop, and a urethane inner lining.

5. The joint wrap of claim 4, wherein one wing on the upper bladder section has a hook material on an end, and one wing on the lower bladder section has a hook material on an end, such that the hook material ends extend past corresponding openings in the cover wings.

6. The joint wrap of claim 5, wherein the cover further comprises a padded hose coupling assembly extension.

7. The joint wrap of claim 6, wherein the first and second tabs have hook material on an end.

8. The joint wrap of claim 7, wherein the first opening in the center body bladder section is a first slit from the upper bladder section to the lower bladder section.

9. The joint wrap of claim 8, wherein the first opening in the center body bladder section further comprises a second slit oriented perpendicular to the first slit.

10. The joint wrap of claim 2, wherein the bladder comprises separate chambers for cooling and compression.

* * * * *